US005871463A

United States Patent [19]
Baker et al.

[11] Patent Number: 5,871,463

[45] Date of Patent: Feb. 16, 1999

[54] SELF-CONTAINED PORTABLE COLON THERAPY MACHINE

[76] Inventors: Mary Ruth Baker; Stuart K. Baker, both of 3130 Thomas Rd., Clearwater, Fla. 34619-3539

[21] Appl. No.: 810,423

[22] Filed: Mar. 4, 1997

[51] Int. Cl.[6] ...................................................... A61M 1/00

[52] U.S. Cl. ............................. 604/27; 604/19; 604/275; 604/276

[58] Field of Search ................................. 604/27, 30, 32, 604/33, 35, 36, 317, 334, 315, 19, 21, 257, 259, 260, 262, 275, 276; 600/563

[56] References Cited

U.S. PATENT DOCUMENTS 2,617,416 11/1952 Condit .
3,044,465 7/1962 Anderson et al. .
4,190,059 2/1980 Halt ........................................ 128/750

*Primary Examiner*—Wynn Wood Coggins
*Assistant Examiner*—Cris L. Rodriguez
*Attorney, Agent, or Firm*—Nixon & Vanderhye

[57] ABSTRACT

The portable self-contained colonic machine includes a generally T-shaped housing having hot and cold water inlets, a mixed water inlet and a drain in a recess below the flange on one side of the machine and a water outlet to the user, a return line inlet and a rinsing outlet in the recess along the opposite side of the machine below the flange. The outlets and inlets lie within the rectilinear confines of the housing. A return line extends linearly from the return line inlet through a view tube and an on/off valve to an outlet port to the drain. The linear extending return line facilitates manual cleaning of the machine.

14 Claims, 3 Drawing Sheets

46
50
76
18
22
66
70
64
24
86
62
74
58
60
63
54
55
61
57
52
PSI
56
61
42
40
38
20

TEMP
MIX
COLD
HOT
TO DRAIN

SELF-CONTAINED PORTABLE COLON THERAPY MACHINE

TECHNICAL FIELD

The present invention relates to colon hydrotherapy machines and particularly to a self-contained hydrotherapy machine which is compact and readily and easily portable.

BACKGROUND

Colonic hydrotherapy machines have been in use for some time and their use is increasing. These machines are designed for colonic irrigation, i.e., the washing out of an individual's intestinal tract. Typically, these machines are permanent, fixed installations located at a therapist's office such that the individual desiring colonic treatment must be referred to that fixed location for treatment. Accordingly, there has developed a need for a portable colon hydrotherapy machine where the machine can be carried by the individual user or brought to the location of the user and, with minimum effort, can be set up and utilized by the user.

DISCLOSURE OF THE INVENTION

In accordance with the present invention, there is provided a self-contained portable colon hydrotherapy machine which is relatively dimensionally small compared with conventional fixed hydrotherapy machines but which contains all of the functions of the fixed machine in a compact portable unit. More particularly, the present invention includes a generally T-shaped housing having recesses on opposite sides of the lower leg of the T-shaped housing and below the opposite ends of the flange of the T-shaped housing. Ports for the various connections of the machine, for example, water inlet and return from the user are provided in the recesses. Significantly, these recesses enable the use of quick connect/disconnect couplings without the various couplings projecting beyond the rectilinear confines of the length, depth and height dimensions of the housing. That is, the various valves, flow conduits, gauges and switches are packaged within this relatively small housing in this unique housing shape which, in turn, affords the advantage of reduced volume, as well as the absence of projecting parts.

The various operating elements of the colonic machine are compactly enclosed within the walls of the housing without affecting the function of the machine, while affording additional advantages. For example, discrete hot and cold water inlets, as well as a hot and cold water mix inlet, are provided through one of the walls of the recesses, enabling the machine for use with discrete hot and cold water taps or with a single mixing faucet, for example, as would typically be found in a home environment. Within the housing, there is provided a mixing valve for mixing the hot and cold water received through the discrete inlets and a mixing block. From the mixing block, the mixed hot and cold water is transmitted through a pressure regulator to an on/off water valve, a three-way block having a temperature sensing probe, a flow control valve with a pressure relief valve and an outlet opening through the wall of the housing for flowing water at a predetermined temperature to a speculum. Housed within the enclosure, there is also provided a view tube forming part of a return line from the speculum to a drain. With the view tube having a backlight within the housing, it will be appreciated that fecal and other matter passing from the patient may be visually inspected. Moreover, by forming the return line as a straight-through line between opposite sides of the machine, cleaning and rinsing of the machine subsequent to use is facilitated.

In a preferred embodiment according to the present invention, there is provided a self-contained portable colonic machine comprising a housing having a plurality of walls defining an enclosure within the walls, the housing having a mixing valve and hot and cold water inlets extending through at least one of the walls for separately supplying hot and cold water to the mixing valve, a mixing block within the enclosure in communication with the mixing valve and having an inlet extending through a wall of the housing for supplying a mix of hot and cold water to the mixing block, a flow control valve within the housing, the mixing block having an outlet for supplying water at a predetermined temperature to the flow control valve, an outlet carried by the housing in communication with the flow control valve for supplying water at the predetermined temperature to a speculum for use in directing water to a user's colon, a return line carried by the housing having a discrete return line inlet and a discrete return line outlet spaced from one another and opening through discrete walls of the housing and a viewing chamber and a drain valve in the return line.

In a further preferred embodiment according to the present invention, there is provided a self-contained portable colonic machine comprising a generally T-shaped housing having a plurality of walls defining an enclosure within the walls and having recesses along opposite sides below a flange of the T-shaped housing and outwardly of a leg of the T-shaped housing, the housing having a water inlet extending through at least one of the walls and in one of the recesses for receiving water, a flow control valve within the housing in communication with the water inlet, an outlet carried by the housing in communication with the flow control valve for supplying water to a speculum for use in directing water to a patient's colon, the water outlet extending through a wall of the housing and in a recess of the housing, a return line carried by the housing having a discrete return line inlet and discrete return line outlet spaced from one another and opening through discrete walls of the housing into respective recesses, the water inlet, the water outlet, the return line inlet and the return line outlet lying substantially within the recesses and within the confines of length, height and depth dimensions of the housing and a viewing chamber and a drain valve in the return line.

Accordingly, it is a primary object of the present invention to provide a self-contained portable colonic hydrotherapy machine which is relatively small in size, light in weight and readily transportable to and from a user or by a user.

BEST MODE FOR CARRYING OUT THE INVENTION

Figure 1:
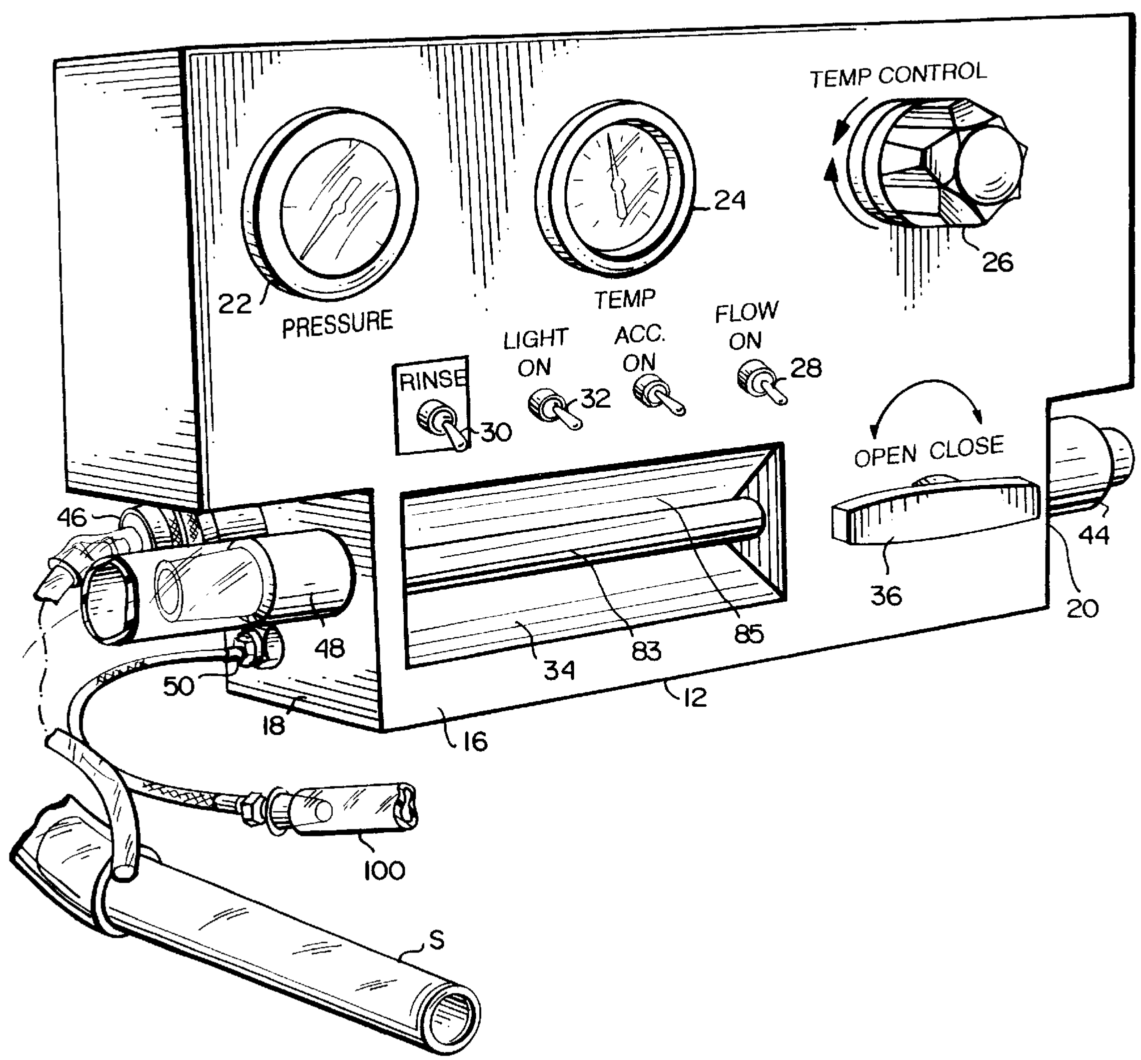
FIG. 1 is a front and right side perspective view of a portable self-contained colonic hydrotherapy machine according to the present invention.
Figure 3:
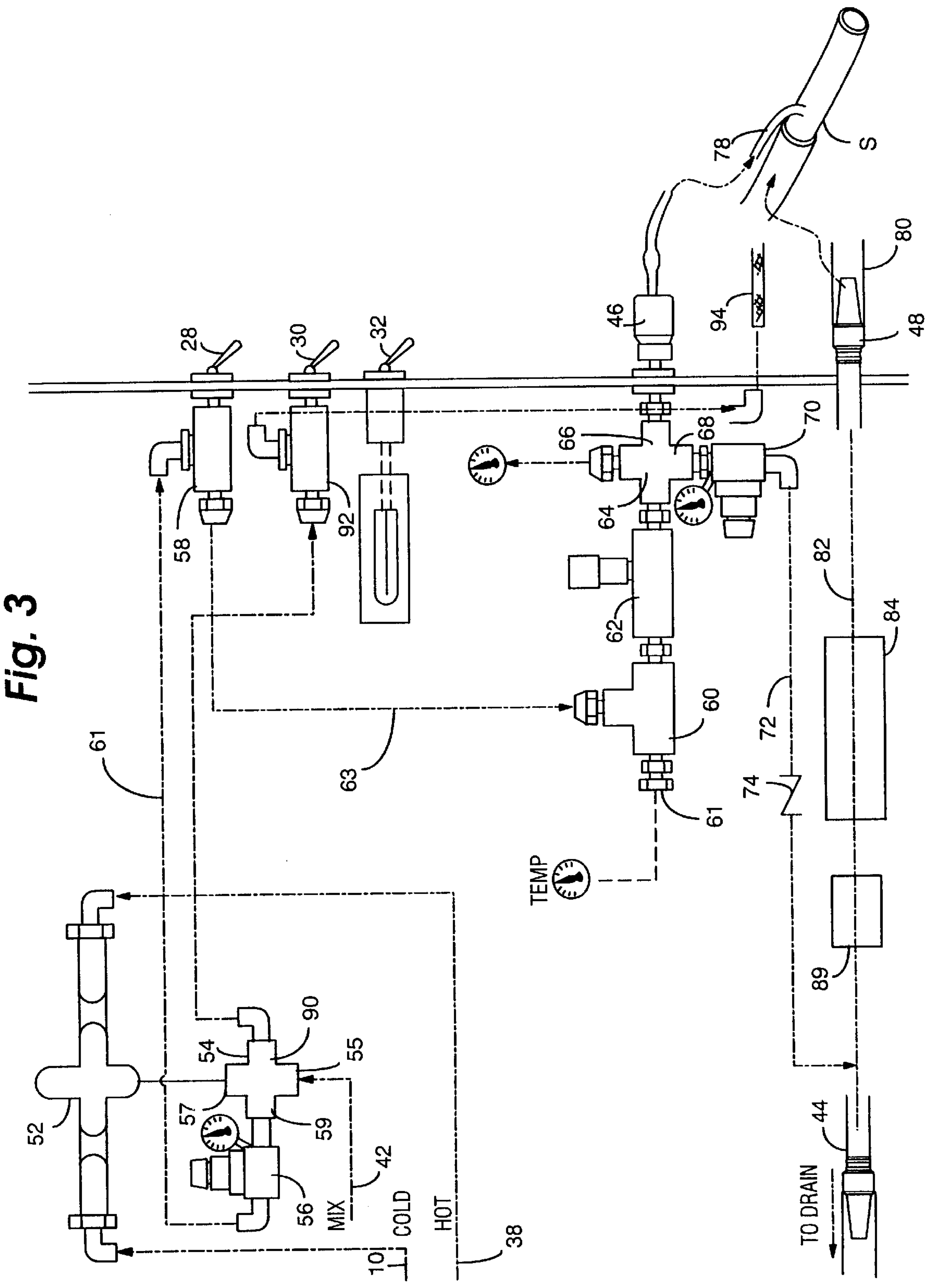
FIG. 3 is a schematic diagram illustrating the various fluid and electric circuits for the machine of FIG. 1.

Before describing the colonic machine hereof, it will be appreciated that the purpose of colonic hydrotherapy is to afford colonic irrigation, i.e., the washing out of the intestinal tract. This is accomplished typically by supplying water at a predetermined temperature to a speculum S (FIGS. 1 and 3). The speculum is initially applied to the patient with an obturator extending through the generally cylindrical speculum to facilitate insertion. Once the speculum is inserted, the obturator is removed and the water flow from the colonic machine may commence. The water flows from the machine through the speculum into the colon. Once the patient is filled, the machine diverts the water to a drain by permitting the water to flow by gravity from the patient through the view chamber and ultimately to the drain. The operation is periodic in that the water is supplied and then turned off for drainage, that cycle being repeated until complete cleansing is effected.

Referring now to FIG. 1, there is illustrated a self-contained portable colonic machine according to the present invention, generally designated 10, and including a housing 12 which is generally T-shaped, having an upper flange 14 and a lower central leg 16 defining recesses 18 and 20 on opposite sides of the leg 16 and below the flange 14. The housing includes a front wall on which various controls and indicators are provided, as set forth below, a top wall, bottom wall, rear wall and side walls. The front wall houses indicators 22 and 24 for indicating the pressure and temperature of the water, respectively. A rotatable knob 26 is also provided for controlling the temperature of the water. Additionally, the front wall also mounts switches for performing various operations, including a flow control on/off switch 28, a rinse switch 30 and an on/off light switch 32 for controlling the light for a view chamber 34. The view chamber 34 is exposed for viewing through the front wall of the housing and it will be appreciated that the view chamber is for purposes of viewing the matter cleansed from the patient's intestinal tract. Additionally, a valve-open and valve-closed handle 36 is provided for filling the patient and discharging water from the patient as discussed below.

Figure 2:
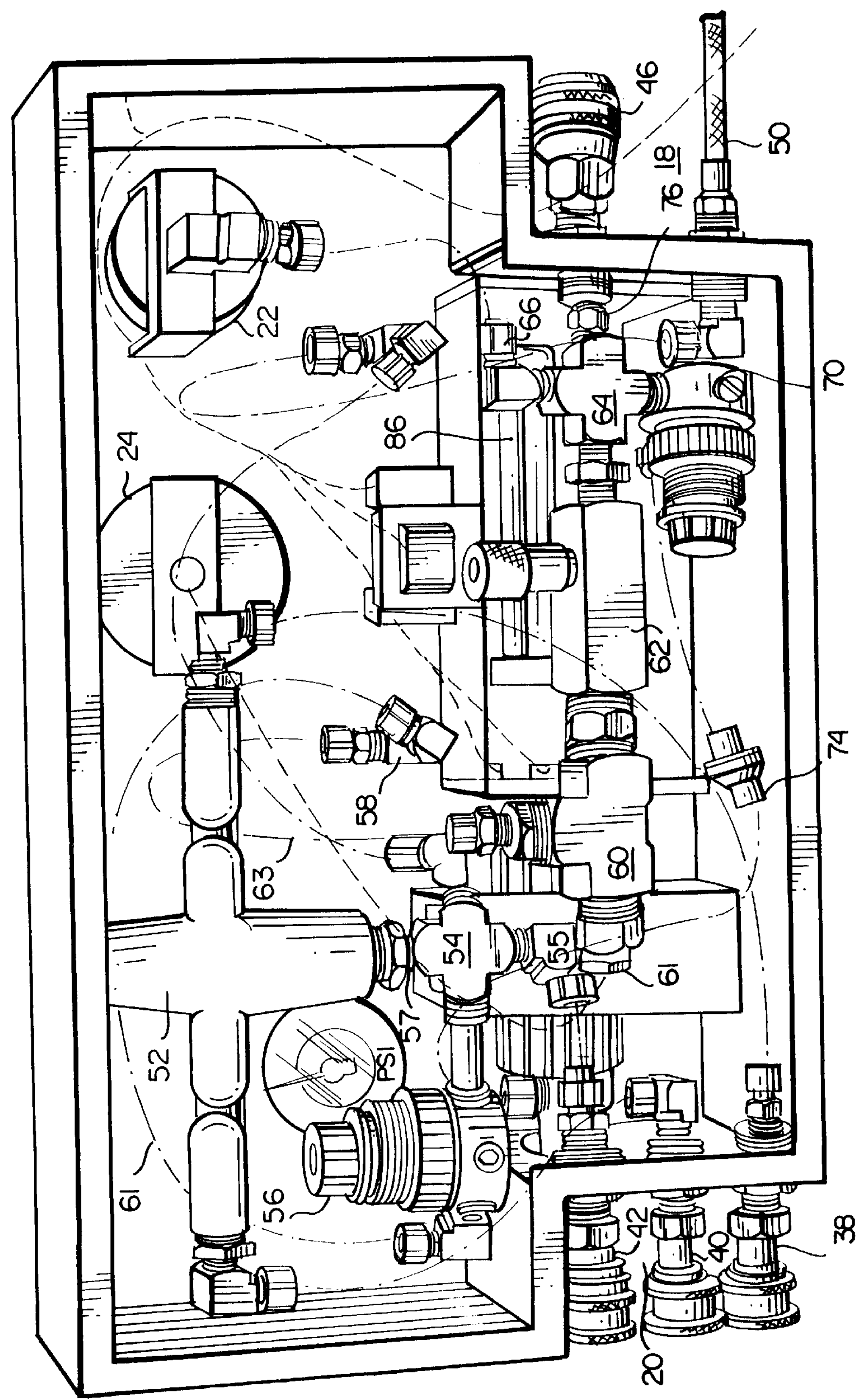
FIG. 2 is a rear perspective view of the machine of FIG. 1 with its back closing plate removed, illustrating the interior of the housing of the machine.

Referring to FIGS. 1 and 2, the various fluid and electrical circuits for the machine will now be described. In the recess 20, as best seen in FIG. 2, there are provided discrete hot and cold water inlet ports 38 and 40 for receiving hot and cold water, respectively, as well as an inlet port 42 for receiving previously mixed hot and cold water at a predetermined temperature. The ports 38, 40 and 42 are provided with quick connect/disconnect type couplings which are of the water shutoff type. That is, when the male and female ends of the coupling are disconnected, a small springloaded valve within the quick connect/disconnect coupling closes and shuts off the flow. In front of the three inlet ports 38, 40 and 42 and illustrated in FIGS. 1 and 3, there is provided a drain outlet port 44 (FIG. 1) for flowing the water to a drain, not shown. On the opposite side of the housing and in recess 18, there is provided an outlet port 46 for supplying water from machine 10 to the speculum S and which employs a similar type of quick connect/disconnect device. Additionally, in recess 18, an inlet port 48 for the return line from the speculum S as well as an additional outlet 50 coupled to a flexible line for use in the rinsing cycle, are provided for purposes to be described. From a review of the drawing figures, it will be appreciated that these various inlet and outlet connections are well within the recesses or have flexible lines such that the lines can be coiled within the recesses. Thus, the connections lie within the rectilinear confines of the length, width and height dimensions of the housing.

Turning now to FIG. 3, the hot and cold water inlets 38 and 40, respectively, are connected on opposite sides of a mixing valve 52 disposed within housing 12. Mixing valve 52 is a conventional valve specifically for mixing hot and cold water supplied from individual taps to a desired temperature. The temperature is controlled by the knob 26 on the face of the housing and can be pre-set to a desired temperature, for example, about 98° F. The valve 52 is provided with a pre-set stop at 100° F. and has an override should a higher temperature be desired. Thus, the mixing valve 52 automatically mixes the water to the desired selected temperature. Water at the predetermined temperature then flows to a mixing block 54. The mixing block 54 has a port 55 for receiving previously blended hot and cold water from inlet port 42, as well as an inlet port 57 for receiving the blended hot and cold water from mixing valve 52. A pressure regulator 56 is in communication with an outlet port 59 of the mixing block 54. The pressure regulator 56, which may be a spring-loaded diaphragm type valve, maintains a nearly constant outlet pressure despite changes in inlet pressure and changes in downstream flow requirements.

As illustrated, the outlet from the pressure regulator 56 is coupled via conduit 61 to an on/off water valve 58 under the control of the on/off switch 28 illustrated in FIG. 1. The outflow from the on/off water valve 58 flows via conduit 63 into a three-way block or T 60 having a temperature probe 61 coupled to the temperature gauge 24. From the block 60, the water flows to a flow control valve 62. The flow control valve 62 regulates the flow of water at the constant pressure delivered by the pressure regulator 56. Thus, the water exits the flow control valve at a constant flow rate. Additionally, the flow control valve serves as a check valve, preventing backflow of water past the flow control valve.

The water from the flow control valve 62 then enters a four-way cross 64. The upper port 66 of the cross 64 is coupled to the pressure gauge 22 disposed on the front wall of the housing. The pressure gauge thus senses the back pressure of the water and, hence, in use is registering the pressure placed on the colon. The lower port 68 of the cross 64 is coupled to a mini-relief valve 70. This valve has a small pressure range, for example, from 0 to 10 psi and is typically set to 2 psi. When the pressure of the system exceeds 2 psi, the mini-relief valve 70 opens, enabling water to flow from the cross 64 through its lower exhaust port 68 past valve 70 and via a drain line 72 and a check valve 74 to a drain. Check valve 74 precludes water or waste matter return flow back into the water manifold system or to the patient from the drainage system. The final port 76 of the cross 64 is connected to the quick connect/disconnect coupling 46 for supplying water at the desired temperature to the inlet 78 of the speculum S.

The speculum S may be any conventional speculum sold on the market. Typically, the speculum includes an obturator to facilitate insertion of the speculum into the patient. Once inserted, the obturator is withdrawn and water may flow into and through the speculum to the patient. The return end of the speculum is coupled via line 80 to the return inlet 48. Inlet 48 is coupled to a return line 82 which passes through a view tube 84 and a water flow open or close valve operated by handle 36. The return line 82 ultimately is in communication with a drain.

The view chamber 34, which includes a clear plastic tube 83, flows through a housing 85 which is essentially V-shaped. A light fixture 86 (FIG. 2) is located behind housing 85 to backlight the view tube. Preferably, the light is a fluorescent lamp which affords sufficient backlighting for viewing with little or no heat production. Consequently, with the clear plastic view tube 83 backlit, view tube 83 affords a means for viewing the fecal and other matter as it discharges from the patient to the drain line.

The operating handle 36 controls the valve 89 in the drain line 82. Consequently, when the handle 36 is moved to an open position, water and fecal matter is permitted to drain from the patient under gravity. When the handle 36 is moved to a closed position, the drain line 82 is closed and the patient is typically being filled.

It is a particular feature of the present invention that the drain line 82 which passes between opposite sides of the machine between the inlet and outlet ports thereof in the recesses 18 and 20 extends linearly through the machine. This facilitates cleaning the machine after use during rinsing operations. To rinse the machine, the mixing block 54 has a port 90 which communicates through an on/off rinse valve 92 with an external rinse line 94. The on/off rinse valve 92 is under the control of switch 30. Consequently, after the machine has been used, and after the speculum has been discarded, the remaining parts of the machine, i.e., the return inlet 48, the view tube 83 and the valve 36 and drain port 44, must be cleaned. Prior to rinsing, an L-shaped adapter, not shown, is attached to the inlet 48. Disinfectant fluid is then poured into a funnel disposed in the L-shaped adapter, filling the view tube completely. The fluid is left in the assembly for a prescribed time. The valve is then placed in an open position and the disinfectant fluid allowed to drain from the system. The L-shaped adapter is then removed and the return line is cleaned by inserting a brush through the inlet 48, the brush containing a disinfectant. The brush is moved back and forth in the drain line 82 its full length between the ports 48 and 44, cleaning the interior of the return line 82. After the brushing is completed, an adapter coupling 100 is applied to the inlet port 48 at the drain line 82 and the handle 36 is moved to a open position. The rinsing system is then connected to the view tube assembly by coupling coupler 100 to the inlet port 48. With the valve handle 36 in an open position, the rinse switch 30 is opened and water from the mixing block is supplied to the rinse tube 94 and, hence, the return line 82 for flow through the return line to the drain. The tube can be filled by manipulating the on/off valve handle 36 between open and closed positions to retain water in the return line 82 for periods of time, as necessary. By returning the valve handle 36 to the open position, the rinse water may be drained. The cycle of rinsing may be repeated as long as necessary.

It will be appreciated that the foregoing has been provided in a compact portable housing having the following generally maximum dimensions: a length of 20 inches, a height of 15 inches and a depth of 5 inches. Preferably, the housing is 19 inches long, 11.5 inches high and 4.5 inches deep. Note also that the couplings and fittings lie well within the rectlinear confines of the length, width and depth dimensions of the housing whereby there is little danger in displacing those fittings by engaging them against other objects. The housing also weighs less than 50 pounds and preferably weighs 40 pounds. Additionally, the straight-through return line affords the advantage of ease of cleaning the portable colonic machine as is necessary if its portability is to be useful.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A self-contained portable colonic machine comprising:

a housing having a plurality of walls defining an enclosure within said walls, said housing having a mixing valve and discrete hot and cold water inlets extending through at least one of said walls for separately supplying hot and cold water to said mixing valve;

a mixing block within said enclosure in communication with said mixing valve and having a first inlet for receiving mixed hot and cold water from said mixing valve and a second inlet extending through a wall of said housing for supplying a pre-mix of hot and cold water to the mixing block;

a flow control valve within said housing;

said mixing block having an outlet for supplying water at a predetermined temperature received by said mixing block from one of said first and second inlets to said flow control valve;

an outlet carried by said housing in communication with said flow control valve for supplying water at said predetermined temperature to a speculum for use in directing water to a user's colon;

a return line carried by said housing having a discrete return line inlet and a discrete return line outlet spaced from one another and opening through discrete walls of said housing; and a viewing chamber and a drain valve in said return line;

said housing being generally T-shaped having an upper flange, a bottom leg below said flange and recesses along opposite sides below said flange and outwardly of said leg of the T-shaped housing, said hot and cold water inlets, said mixing block inlet, said water supply outlet, said return line inlet and said return line outlet lying substantially within said recesses and within the confines of length, height and depth dimensions of said housing.

2. A machine according to claim 1 wherein said housing is generally rectilinear having length, height and depth dimensions no greater than 20, 15 and 5 inches, respectively.

3. A machine according to claim 2 weighing no more than 40 pounds.

4. A machine according to claim 1 wherein said housing is generally T-shaped having recesses along opposite sides below a flange of the T-shaped housing and outwardly of a leg of the T-shaped housing, said hot and cold water inlets, said mixing block inlet, said water supply outlet, said return line inlet and said return line outlet lying substantially within said recesses and within the confines of the length, height and depth dimensions of said housing.

5. A machine according to claim 1 wherein said return line passes linearly through said housing with said return line inlet extending through one wall of said housing and said return line outlet extending through an opposite wall of said housing.

6. A machine according to claim 5 wherein said housing is generally T-shaped having recesses along opposite sides below flanges of the T-shaped housing and outwardly of a leg of the T-shaped housing, said return line inlet and said return line outlet lying within said recesses, respectively, along opposite sides of said housing.

7. A self-contained portable colonic machine comprising:

a generally T-shaped housing having a plurality of walls defining an enclosure within said walls, said walls defining an upper flange and a bottom leg of said T-shaped housing below said flange, said housing having recesses along opposite sides below said flange of the T-shaped housing and outwardly of said leg of the T-shaped housing, said housing having a water inlet extending through at least one of said walls and in one of said recesses for receiving water;

a flow control valve within said housing in communication with said water inlet;

an outlet carried by said housing in communication with said flow control valve for supplying water to a speculum for use in directing water to a patient's colon, said water outlet extending through a wall of said housing and in a recess of said housing;

a return line carried by said housing having a discrete return line inlet and discrete return line outlet spaced from one another and opening through discrete walls of said housing into respective recesses, said water inlet, said water outlet, said return line inlet and said return line outlet lying substantially within said recesses and within the confines of length, height and depth dimensions of said housing; and a viewing chamber and a drain valve in said return line; said return line passing linearly through said housing with said return line inlet extending through one wall of said housing and said return line outlet extending through an opposite wall of said housing.

8. A machine according to claim 7 wherein said housing is generally rectilinear having length, height and depth dimensions no greater than 20, 15 and 5 inches, respectively.

9. A machine according to claim 8 weighing no more than 40 pounds.

10. A machine according to claim 7 wherein said return line passes linearly through said housing with said return line inlet extending through one wall of said housing and said return line outlet extending through an opposite wall of said housing, said one wall and said opposite wall defining in part walls of said recesses, respectively.

11. A machine according to claim 7 wherein said return line inlet and said return line outlet lie within said recesses, respectively, along opposite sides of said housing.

12. A self-contained portable colonic machine comprising:

a housing having a plurality of walls defining an enclosure within said walls, said housing having a mixing valve and hot and cold water inlets extending through at least one of said walls for separately supplying hot and cold water to said mixing valve;

a mixing block within said enclosure in communication with said mixing valve and having an inlet extending through a wall of said housing for supplying a mix of hot and cold water to the mixing block;

a flow control valve within said housing;

said mixing block having an outlet for supplying water at a predetermined temperature to said flow control valve;

an outlet carried by said housing in communication with said flow control valve for supplying water at said predetermined temperature to a speculum for use in directing water to a user's colon;

a return line carried by said housing having a discrete return line inlet and a discrete return line outlet spaced from one another and opening through discrete walls of said housing; and a viewing chamber and a drain valve in said return line;

said housing being generally T-shaped having an upper flange, a bottom leg below said flange and recesses along opposite sides thereof below said flange and outwardly of said leg of the T-shaped housing, said hot and cold water inlets, said mixing block inlet, said water supply outlet, said return line inlet and said return line outlet lying substantially within said recesses and within the confines of length, height and depth dimensions of said housing.

13. A machine according to claim 12 wherein said return line passes linearly through said housing with said return line inlet extending through one wall of said housing and said return line outlet extending through an opposite wall of said housing.

14. A machine according to claim 13 wherein said return line inlet and said return line outlet extend within said recesses, respectively.

* * * * *